United States Patent [19]

Kunz

[11] 4,368,327
[45] Jan. 11, 1983

[54] PROCESS FOR THE PREPARATION OF 3-(N-ARYLAMINO)-TETRA-HYDROTHIO-PHEN-2-ONE DERIVATIVES

[75] Inventor: Walter Kunz, Oberwil, Switzerland

[73] Assignee: Ciba-Geigy Corporation, Ardsley, N.Y.

[21] Appl. No.: 279,124

[22] Filed: Jun. 30, 1981

Related U.S. Application Data

[63] Continuation-in-part of Ser. No. 176,821, Aug. 8, 1980, abandoned.

[51] Int. Cl.$^3$ ............... C07D 233/00; C07D 333/16
[52] U.S. Cl. .................................. 548/262; 549/60; 549/63; 424/269; 424/275
[58] Field of Search ..................... 549/62, 63, 60; 548/262

[56] References Cited

PUBLICATIONS

"Arkiv. för Kemi", vol. 8, No. 47, pp. 457–461, Schohe.

*Primary Examiner*—Alan Siegel
*Attorney, Agent, or Firm*—Karl F. Jorda

[57] ABSTRACT

A process for the preparation of 3-(arylamino)-tetrahydrothiophen-2-one derivatives is described in which the corresponding 3-(N-arylamino)-tetrahydrofuran-2-one derivatives are reacted with salts of thiocarboxylic acids. 3-(N-Arylamino)-tetrahydrothiophen-2-one derivatives are usable fungicides for plants.

11 Claims, No Drawings

PROCESS FOR THE PREPARATION OF 3-(N-ARYLAMINO)-TETRA-HYDROTHIOPHEN-2-ONE DERIVATIVES

CROSS-REFERENCE

This application is a continuation-in-part of my pending application Ser. No. 176,821 filed Aug. 8, 1980 now abandoned.

The present invention relates to a novel process for the preparation of 3-(N-arylamino)-tetrahydrothiophen-2-one derivatives by reacting 3-(N-arylamino)-tetrahydrofuran-2-one derivatives with salts of thiocarboxylic acids. 3-(N-arylamino)-tetrahydrothiophen-2-one derivatives have been disclosed as fungicides in German Offenlegungsschrift No. 2,845,454 (1979) and U.S. Pat. No. 4,165,322 (1979).

In these references it is proposed that 3-(N-arylamino)-tetrahydrothiophen-2-one derivatives can be prepared by reacting N-arylamines with 3-halogenotetrahydrothiophen-2-one derivatives. The latter can, if desired, be N-acylated with acyl halides.

This known procedure is involved and not very suitable for an industrial preparation, especially because of the use of 3-halogeno-tetrahydrothiophen-2-one derivatives as the starting materials, since the preparation of these derivatives via the tetrahydrofuran-2-one derivatives can be effected only with a great deal of preparative effort, with loss of yield or with extensive pollution of the environment.

As has been disclosed, for example, in CA. 84, 17124 a [Japan Kokai 75/70,354 (31.10.1973)], halogenation of tetrahydrothiophen-2-one yields in the main 3,3-dihalogeno-tetrahydrothiophen-2-one and yields the desired 3-monohalogeno-tetrahydrothiophen-2-one only in 13% yield.

The tetrahydrothiophen-2-one derivatives themselves can indeed be prepared by a large number of known methods, but all of these methods have certain disadvantages.

For example, it has been disclosed [Houben-Weyl 6/2, 851 and German Patent Specification 809,557 (1949) BASF] that tetrahydrothiophen-2-one can be prepared by reacting tetrahydrofuran-2-one with carbon disulfide.

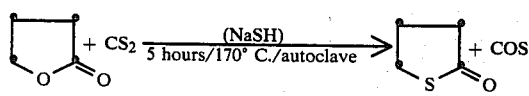

This reaction not only has the disadvantage that highly toxic $CS_2$ is used as a starting material and that COS, which is also toxic, is formed; it can also be carried out only under high pressures and with high expenditure of energy.

Another known procedure [Toland and Campbell, J. Org. Chem. 28, 3,124 (1963)] for the preparation of tetrahydrothiophen-2-ones uses dicarboxylic acid anhydrides, for example succinic anhydride, and hydrogen sulfide, which is toxic, as the starting materials:

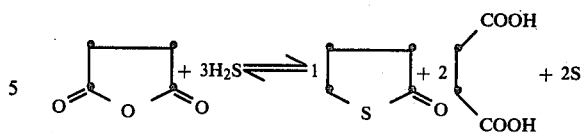

With this reaction only one molecule of the end product is formed per 3 molecules of the starting material, which corresponds to a loss in yield of 2/3.

According to Reppe [Liebigs Annalen der Chemie 596, 173 (1955)], tetrahydrothiophen-2-one can be prepared from tetrahydrofuran-2-one:

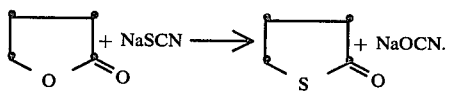

Toxic thiocyanide is used in this reaction and readily soluble cyanate, which is an environmental hazard, is formed.

Furthermore, it has been disclosed [Korte & Lohmer, Chem. Ber. 90, 1,290 (1957)] that tetrahydrothiophen-2-one can also be prepared in a complex, multi-stage process by first adding thioacetic acid onto vinylacetic acid, then subjecting the acetyl product to alkaline hydrolysis to give γ-mercaptobutyric acid and finally cyclising the acid at high temperature to give tetrahydrothiophen-2-one.

The reaction of tetrahydrofuran-2-one with alkali metal salts of thioacetic acid [Schotte, Arkiv Kemi 8, 457–61; (C.A. 51, 1838 h)], which is the reaction most closely comparable to the process of the present invention, results in opening of the tetrahydrofuran ring:

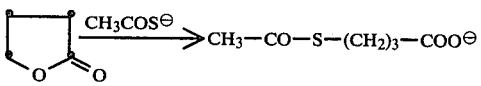

The γ-acetylmercapto-butyric acid salt is formed and this can be converted to the free acid by neutralisation.

It has now been found, completely surprisingly, that when 3-(N-arylamino)-tetrahydrofuran-2-one derivatives are used in place of tetrahydrofuran-2-one and the reaction is carried out with the salt of a thiocarboxylic acid, it is not the open-chain γ-acetylmercaptoacetic acid derivative, which according to Schotte would be expected, which is obtained but, in a particularly simple manner and in high yield, 3-(N-arylamino)-tetrahydrothiophen-2-one derivatives.

The process according to the present invention relates to the preparation of 3-(N-arylamino)-tetrahydrothiophen-2-one derivatives of the general formula A:

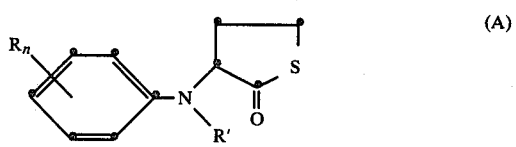

in which the heterocyclic five-membered ring is unsubstituted or monosubstituted or polysubstituted by $C_1$–$C_4$-alkyl, n is an integer from 0 to 5, R signifies a number of identical or different substituents other than hydrogen, selected from $C_1$-$C_{12}$-alkyl, $C_1$-$C_{12}$-alkoxy, halogen, nitro, and —CH$_2$—X—R", and whereby two substituents R which are adjacent to one another may also form together with the phenyl ring a naphthyl group, and X is oxygen or sulfur and R" is unsubstituted, monosubstituted or polysubstituted $C_1$-$C_{12}$-alkyl, unsubstituted, monosubstituted or polysubstituted phenyl or unsubstituted, monosubstituted or polysubstituted benzyl and in the three cases mentioned the possible substituents independently of one another are selected from the series lower alkyl, lower alkoxy, halogen or nitro, and R' is hydrogen or the group —CO—R''', in which R''' is a non-halogenated aliphatic, heterocyclic-aliphatic or heterocyclic radical or in which R''' is an aromatic or araliphatic radical which is unsubstituted or substituted in the aromatic moiety by halogen and in which the heterocyclic structure in each case contains one or more N, O and/or S atoms and an aliphatic chain can be interrupted one or more times by oxygen, sulfur, or nitrogen, and comprises reacting a compound of the formula B:

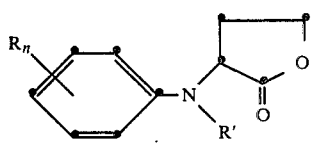

(B)

in which the possible substituents are as defined under formula A, at temperatures of about +15° to +200° C. with a salt of a thiocarboxylic acid.

Lower alkyl or the lower alkyl moiety of another substituent is to be understood as meaning a straight-chain or branched alkyl radical having not more than 6 carbon atoms, for example methyl, ethyl, propyl or butyl, and also their isomers, for example isopropyl, isobutyl, tert.-butyl and the like. In the specification, halogen is fluorine, chlorine, bromine or iodine, preferably fluorine, chlorine or bromine.

Typical examples of araliphatic substituents are benzyl, phenylethyl, phenylethenyl and 2,2-diphenylethenyl. Heterocyclic-aliphatic radicals are, for example, triazolylmethyl, imidazolylethyl and 2-methylpyridyl.

Heterocyclic substituents and heterocyclic moieties of substituents are derived, in particular, from five-membered or six-membered ring systems and can carry one or more double bonds in the ring or can be completely hydrogenated. Advantageous radicals are: isoxazole, furan, tetrahydrofuran, α-pyran, γ-pyran, dihydropyran, thiophene, tetrahydrothiophene, pyrrole, pyrrolidine, pyrazole, imidazole, triazole, piperidine, piperazine, pyridine, pyrimidine, pyridazine, pyrazine, triazine, morpholine, thiazine, thiomorpholine and systems having a fused benzene ring, such as quinoline, isoquinoline, 1,2-dihydroquinoline, acridine, chromene, chroman, indole, benzofuran, benzothiophene and benzimidazole.

The term salt is to be understood as meaning, in particular, a metal salt, ammonium salt, hydrazinium salt or other salt of a quaternised organic N-containing base.

The process according to the invention is used in particular for the preparation of 3-(N-anilino)-tetrahydrothiophen-2-one derivatives of the formula I:

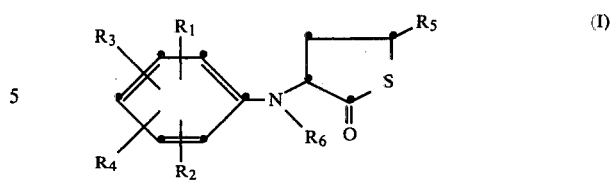

(I)

in which $R_1$ is hydrogen, $C_1$-$C_4$-alkyl, $C_1$-$C_4$-alkoxy or halogen, $R_2$ is hydrogen, $C_1$-$C_4$-alkyl, $C_1$-$C_4$-alkoxy, halogen or nitro, $R_3$ is hydrogen, $C_1$-$C_4$-alkyl, $C_1$-$C_4$-alkoxy, halogen or the group CH$_2$—X—R$_8$, in which $R_8$ is $C_1$-$C_4$-alkyl, phenyl or benzyl and X is oxygen or sulfur and $R_4$ is hydrogen or $C_1$-$C_4$-alkyl, $R_5$ is hydrogen and $R_6$ is hydrogen or the group —CO—R$_7$, in which $R_7$ is a saturated or unsaturated aliphatic hydrocarbon radical which has not more than 4 carbon atoms or is an alkylthioalkyl or alkoxyalkyl group having 2 to 5 carbon atoms, a 2-furyl or 2-tetrahydrofuryl group which is substituted by halogen or unsubstituted, or a 1,2,4-triazolylmethyl or cyclopropyl group, and comprises reacting a 3-(N-anilino)tetrahydrofuran-2-one-derivative of the formula II

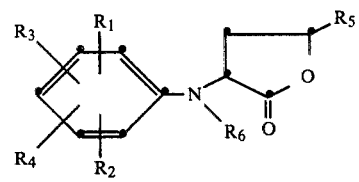

(II)

in which $R_1$, $R_2$, $R_3$, $R_4$, $R_5$ and $R_6$ are as defined under formula I, with a thiocarboxylic acid salt of the formula III:

R—COSX (III)

in which R is a substituted or unsubstituted alkyl or aryl group and X is a metal ion or an ammonium ion.

The majority of the starting compounds of the formula II have been disclosed in the following publications: German Offenlegungsschrift No. 2,804,299, German Offenlegungsschrift No. 2,845,464 and German Patent Specification No. 4,165,322. Their preparation is described in these publications. Intermediates which have not been described previously are prepared analogously or are described in U.S. Patent Application Ser. No. 138,066.

Salts of aliphatic and aromatic thiocarboxylic acids are generally known or are prepared by methods which are generally known.

It is found, suprisingly, that when a 3-(N-arylamino)-tetrahydrofuran-2-one is reacted with a salt of a thiocarboxylic acid the structural pattern of the tetrahydrofuranone ring is retained and only a formal oxygen/sulfur exchange takes place. This course of reaction is completely contrary to expectations and yields the desired thio compounds of the formula A or I in a simple reaction.

3-(N-Arylamino)-tetrahydrothiophen-2-one derivatives can thus be prepared in good yields using readily accessible, inexpensive starting materials and in a very simple and economical manner, which does not give rise to environmental pollution.

It is advantageous to carry out the reaction of 3-(N-arylamino)-tetrahydrofuran-2-one derivatives of the formulae B or II with salts of thiocarboxylic acids in the presence of an organic solvent. Suitable organic solvents are those in which the salts of the thiocarboxylic acids have adequate solubility and which are inert towards the starting materials. Suitable solvents are in particular aprotic solvents, and amongst these those with polar character. Examples of advantageous solvents are: amides, preferably N-alkylated amides, such as N,N-dimethylformamide, N,N-dimethylacetamide, N,N-diethylacetamide, N,N-dimethylmethoxyacetamide and hexamethylphosphoric acid triamide; sulfoxides, such as dimethylsulfoxide and diethylsulfoxide; sulfones, such as tetrahydrothiophene 1,1-dioxide; ethylene glycol diethers and monoethers and diethylene glycol diethers and monoethers, each having 1–4 C atoms in the alkyl moieties, such as ethylene glycol dimethyl ether, ethylene glycol diethyl ether and ethylene glycol di-n-butyl ether, diethylene glycol diethyl ether and diethylene glycol di-n-butyl ether, ethylene glycol monomethyl ether and diethylene glycol monomethyl ether; ether-like compounds, such as dioxan, tetrahydrofuran and tetrahydropyran, and mixtures of such solvents with one another.

If longer reaction times are accepted, less polar and non-polar organic solvents can also be employed; in this case the addition of a conventional phase transfer catalyst proves advantageous.

Examples of such catalysts are: tetraalkylammonium halides, tetraalkylammonium hydrogen sulfates or tetraalkylammonium hydroxides, such as tetrabutylammonium chloride, tetrabutylammonium bromide and tetrabutylammonium iodide; triethylbenzylammonium chloride and triethylbenzylammonium bromide; tetrapropylammonium chloride, tetrapropylammonium bromide and tetrapropylammonium iodide and the like. Phosphonium salts can also be used as phase transfer catalysts.

The reaction of compounds of the formulae B or II with salts of thiocarboxylic acids takes a reaction time of up to fifty hours, depending on the reaction temperature. In most cases, reaction times of one to twenty hours suffice.

The reaction temperatures can preferably be between +50° and +200° C., and a temperature range of +100° to +150° C. is particularly preferred.

Suitable thiocarboxylic acid salts of the formula III:

R—COSX   (III)

are salts of the elements of principal groups one to four and of the elements of sub-groups one to eight, especially the alkali metal salts and alkaline earth metal salts, preferably the alkali metal salts. Further very suitable salts are substituted and unsubstituted ammonium salts, for example thiocarboxylic acid salts containing the cations: $NH_4^{\oplus}$, $NH_3(alkyl)^{\oplus}$, $NH_2(alkyl)_2^{\oplus}$, $NH(alkyl)_3^{\oplus}$ or $N(alkyl)_4^{\oplus}$, in which the alkyl moiety contains 1 to 12 carbon atoms. Suitable salt-forming thiocarboxylic acids are, for example, substituted and unsubstituted aliphatic and aromatic thiocarboxylic acids, for example thiobenzoic acid, phenylthioacetic acid, diphenylthioacetic acid, thioacetic acid, thiopropionic acid, thiobutyric acid, thiovaleric acid, thionaphthoic acid and the like. Aliphatic thiocarboxylic acids are preferred, especially those in which the alkyl moiety has not more than 6 carbon atoms.

Examples of such salts are: $CH_3COS^{\ominus}K^{\oplus}$, $CH_3COS^{\ominus}Na^{\oplus}$, $C_2H_5COS^{\ominus}K^{\oplus}$, $C_6H_5COS^{\ominus}Na^{\oplus}$, $CH_3COS^{\ominus}NH_4^{\oplus}$, $C_2H_5COS^{\ominus}NH_4^{\oplus}$ and $CH_3COS^{\ominus}N(n{-}C_4H_9)_4^{\oplus}$.

Under certain circumstances it can prove advantageous to carry out the preparation process under an atmosphere of an inert gas, for example under nitrogen, and in solvents which have been rendered absolutely dry.

PREPARATION EXAMPLES

EXAMPLE 1

Preparation of:

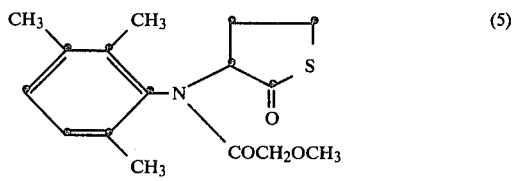

(5)

3-[N-(methoxyacetyl)-N-(2,3,6-trimethylphenyl)]-aminotetrahydrothiophen-2-one 14.5 g (0.05 mol) of 2-[N-(methoxyacetyl)-N-(2,3,6-trimethylphenyl)-amino]-tetrahydrofuran-2-one and 7 g (0.05 mol) of potassium thioacetate are dissolved in 50 ml of dimethylformamide, under a nitrogen atmosphere, and the solution is stirred for 4 hours at 150° C. After stripping off the solvent in vacuo, the reaction mixture is poured into ice-water and extracted with methylene chloride. The combined extracts are dried over sodium sulfate and filtered, the filtrate is concentrated in vacuo and diethyl ether/petroleum ether is added. 10.5 g (68.4% of theory) of colourless 3-[N-(methoxyacetyl)-N-(2,3,6-trimethylphenyl)-amino]-tetrahydrothiophen-2-one crystallise out from the solution. Melting point 86°–90° C.

EXAMPLE 2

Preparation of

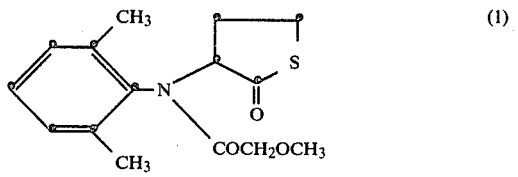

(1)

3-[N-(methoxyacetyl)-N-(2,6-dimethylphenyl)]-aminotetra hydrothiophen-2-one 110.8 g (0.4 mol) of 3-[N-(methoxyacetyl)-N-(2,6-dimethylphenyl)-amino]-tetrahydrofuran-2-one and 39.4 g (0.4 mol) of sodium thioacetate are dissolved in 500 ml of dimethylformamide under a nitrogen atmosphere, and the solution is stirred for 18 hours at 100° to 110° C. After removing the solvent in vacuo, the reaction mixture is poured into ice-water and extracted with methylene chloride. The combined extracts are dried over sodium sulfate and filtered, the filtrate is concentrated in vacuo and diethyl ether is added. 58.4 g (49.8% of theory) of colourless 3-[N-(methoxyacetyl)-N-(2,6-dimethylphenyl)-amino]-tetrahydrothiophen-2-one crystallise out from the solution. Melting point 96°–98° C.

EXAMPLE 3

Preparation of:

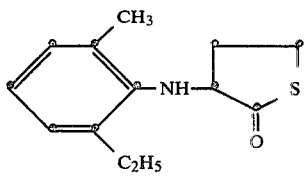
(18)

3-N-(2-methyl-6-ethylphenyl)-amino-tetrahydrothiophen-2-one (a) 11 g (0.05 mol) of N-(2-methyl-6-ethylphenyl)amino-tetrahydrofuran-2-one and 4.7 g (0.05 mol) of ammonium thioacetate are stirred in 80 ml of dimethylsulfoxide at 90° to 100° C. After cooling, the solution is poured into ice-water and extracted with methylene chloride. The combined extracts are repeatedly washed with water, dried over sodium sulfate and filtered and the filtrate is concentrated. Distillation of the residue under a high vacuum yields 5.7 g (48.5% of theory) of colourless N-(2-methyl-6-ethylphenyl)-amino-tetrahydrothiophen-2-one. Boiling point 167°–173° C. under 0.5 mm Hg.

(b) 11 g (0.05 mol) of N-(2-methyl-6-ethylphenyl)amino-tetrahydrofuran-2-one and 6.6 g (0.05 mol) of potassium thioacetate are dissolved in 200 ml of diethylene glycol dimethyl ether and the solution is stirred for 20 hours at 150° C. After cooling, the mixture is poured into ice-water and extracted with methylene chloride. The combined extracts are washed repeatedly with water, dried over sodium sulfate and filtered and the filtrate is concentrated. After distillation under a high vacuum, the residue yields 5.2 g (44.2% of theory) of N-(2-methyl-6-ethylphenyl)-amino-tetrahydrothiophen-2-one. Boiling point 160°–165° C. under 0.45 mm Hg.

EXAMPLE 4

Preparation of an intermediate product:
(a):

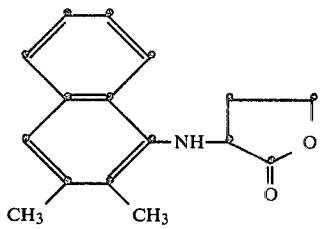

3-[N-(2,3-dimethyl-α-naphthyl)]-amino-tetrahydrofuran-2-one 114.3 g of 2,3-dimethyl-α-naphthylamine, 143.6 g of 3-bromo-butyrolactone and 78.4 g of sodium carbonate are suspended in 400 ml of dimethylformamide. The dark colored suspension is stirred for 15 hours at 75° C. After cooling 300 ml of ethylacetate are added thereto and the reaction mixture is sucked off. The filtrate is evaporated and the residue obtained is washed with diethyl ether and treated with some milliliters of a mixture of isopropanol/acetone (1:1), whereby crystallisation occurs. The thus obtained crystals of the intermediate product have a melting point of 125°–127° C.

(b) Preparation of:

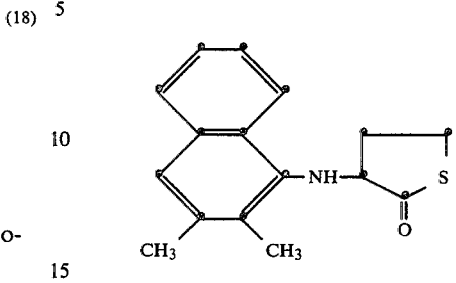

3-[N-(2,3-dimethyl-α-naphthyl)]-amino-tetrahydrothiophen-2-one 12.2 g of the product obtained according to method (a) and 7.2 g of potassium thioacetate (CH₃—CO—SK) are suspended in 60 ml of dimethylformamide. The reaction mixture is stirred for 5 hours at 105°–110° C. and is concentrated in high vacuo. The residue is poured into ice-water and extracted with methylene chloride. The combined extracts are washed with water, dried over sodium sulfate and filtered. The filtrate is concentrated. The oily residue is purified by a silicagel column using chloroform/diethylether (1:1) as the eluant. The clear solution is concentrated whereby the desired product crystallizes, m.p. 81°–84° C.

EXAMPLE 5

Preparation of:

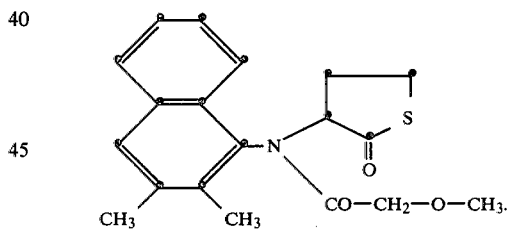

3-[N-(2,3-dimethyl-α-naphthyl)]-N-(methoxyacetyl)-aminotetrahydrothiophen-2-one 9,7 g of 3-[N-(2,3-dimethyl-α-naphthyl)-N-(methoxyacetyl)]-amino-tetrahydrofuran-2-one (obtained by acylation of the intermediate product resulting from Example 4a with e.g. methoxy acetic acid chloride) and 4.1 g of potassium thiocarbonate are suspended in 40 ml of dimethylformamide. The reaction mixture is stirred for 5.5 hours at 105°–110° C. and is concentrated in vacuo. Following the elaboration method of Example 4b the crystallized end product is obtained, m.p. 140°–144° C.

EXAMPLE 6

Preparation of:

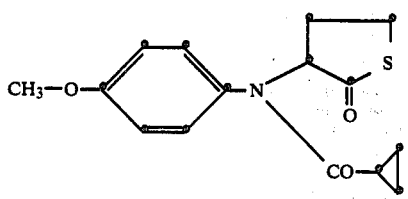

3-[N-(cyclopropylcarbonyl)-N-(4-methoxyphenyl)]-
aminotetrahydrothiophen-2-one 7.2 g of 3-[N-(cyclopropylcarbonyl)-N-(4-methoxyphenyl)]-amino-tetrahydrofuran-2-one (obtained by first reaction of 4-methoxyaniline and 3-bromo-butyrolactone and further acylation of the resulting intermediate product with e.g. cyclopropancarbonic acid chloride in the conventional manner) and 3.7 g of potassium thioacetate are suspended in 30 ml of dimethylformamide. The reaction mixture is stirred for 5 hours at 105°–110° C., concentrated in vacuo and elaborated following the method of Example 4b above. The crystallized end product has a melting point of 109°–112° C.

EXAMPLE 7

Preparation of:

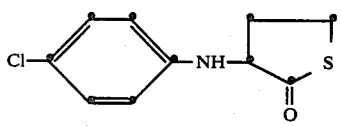

3-N-(4-chlorophenyl)-amino-tetrahydrothiophen-2-one 15.0 g of 3-N-(4-chlorophenyl)-amino-tetrahydrofuran-2-one and 10.1 g of potassium thioacetate are mixed with 70 ml of dimethylformamide. The reaction mixture is stirred and heated for 11 hours to 110° C., concentrated in vacuo and elaborated according to the method of Example 4b above. The end product is obtained in crystals, m.p. 86°–90° C.

The compounds of the formula I:

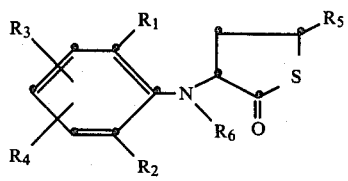

indicated below can, for example, be prepared correspondingly. Where a side chain $R_6 = $ -CO-haloaliphat occurs, the compound in question is preferably being prepared firstly in form of the non-acylated intermediate product having $R_6 = $ hydrogen and subsequent acylation with a carbonic acid of the formula:

HO—CO—haloaliphat or its acid halide, acid anhydride or acid ester in the conventional manner. In some cases, however, the conversion of the tetrahydrofuranone moiety into the tetrahydrothiophenone moiety can also be accomplished in the presence of a haloaliphatic side chain $R_6$.

| Compound No. | $R_1$ | $R_2$ | $R_3$ | $R_4$ | $R_5$ | $R_6$ | Physical constants Melting point/boiling point [°C.] |
|---|---|---|---|---|---|---|---|
| 1 | $CH_3$ | $CH_3$ | H | H | H | $COCH_2OCH_3$ | Melting point 96–98 |
| 2 | $CH_3$ | $CH_3$ | 3-$CH_3$ | 5-$CH_3$ | H | $COCH_2OCH_3$ | Melting point 123–125 |
| 3 | $CH_3$ | $CH_3$ | H | H | H | H | Boiling point 140–145 (0.4 mm Hg) |
| 4 | $CH_3$ | $CH_3$ | 3-$CH_3$ | 5-$CH_3$ | H | CO-oxiranyl | Melting point 205–206 |
| 5 | $CH_3$ | $CH_3$ | 3-$CH_3$ | H | H | $COCH_2OCH_3$ | Melting point 86–90 |
| 6 | $CH_3$ | $CH_3$ | H | H | H | CO-oxiranyl | Melting point 125–127 |
| 7 | $CH_3$ | $CH_3$ | 3-$CH_3$ | H | H | H | Boiling point 173–183 (0.7 mm Hg) |
| 8 | $CH_3$ | $CH_3$ | 3-$CH_3$ | H | H | CO-oxiranyl | Resin |
| 9 | $CH_3$ | $CH_3$ | 3-$CH_2O$—s.$C_4H_9$ | H | H | $COCH_2OCH_3$ | Resin |
| 10 | $CH_3$ | $CH_3$ | 3-$CH_2O$—s.$C_4H_9$ | H | H | H | Resin |
| 11 | $CH_3$ | $CH_3$ | 3-$CH_2O$—Benzyl | H | H | H | Resin |
| 12 | $CH_3$ | $CH_3$ | 3-$CH_2O$—Benzyl | H | H | H | Resin |
| 13 | $C_2H_5$ | $C_2H_5$ | H | H | H | $COCH_2OCH_3$ | Melting point 51–54 |
| 14 | $CH_3$ | $CH_3$ | H | H | H | CO—Cyclopropyl | Melting point 115–117 |
| 15 | H | H | H | H | H | CO—Cyclopropyl | Melting point 81–83 |
| 16 | H | H | H | H | H | H | Boiling point |

-continued

| Compound No. | $R_1$ | $R_2$ | $R_3$ | $R_4$ | $R_5$ | $R_6$ | Physical constants Melting point/boiling point [°C.] |
|---|---|---|---|---|---|---|---|
| 17 | $C_2H_5$ | $C_2H_5$ | H | H | H | CO—Cyclopropyl | 145–160 (0.5 mm Hg) Melting point 130–133 |
| 18 | $CH_3$ | $C_2H_5$ | H | H | H | H | Boiling point 167–173 (0.5 mm Hg) |
| 19 | $CH_3$ | $C_2H_5$ | H | H | H | $COCH_2OCH_3$ | Melting point 125–133 |
| 20 | $C_2H_5$ | $C_2H_5$ | H | H | H | H | Boiling point 162–173 (0.7 mm Hg) |
| 21 | $CH_3$ | $CH_3$ | 3-$CH_2OCH_3$ | H | H | $COCH_2OC_2H_5$ | Resin |
| 22 | $CH_3$ | $CH_3$ | 3-$CH_2OCH_3$ | H | H | $COCH_2Cl$ | Resin |
| 23 | $CH_3$ | $CH_3$ | 3-$CH_2OCH_3$ | H | H | H | Boiling point 187–194 (0.5 mm Hg) |
| 24 | $CH_3$ | $CH_3$ | 3-$CH_3$ | H | H | CO—(2,3-dihydrofuryl) | Melting point 126–128 |
| 25 | $CH_3$ | $CH_3$ | 3-$CH_3$ | H | H | CO—Cyclopropyl | Melting point 130–132 |
| 26 | $CH_3$ | $CH_3$ | 3-$CH_3$ | H | H | $COCH_2Cl$ | Melting point 106–108 |
| 27 | $CH_3$ | $CH_3$ | H | H | H | CO—(2,3-dihydrofuryl) | Melting point 175–177 |
| 28 | $CH_3$ | $CH_3$ | H | H | H | $COCH_2Cl$ | Melting point 134–136 |
| 29 | $CH_3$ | $CH_3$ | H | H | H | $COCH_2OC_2H_5$ | Melting point 91–92 |
| 30 | $CH_3$ | $CH_3$ | H | H | H | CO—Cyclopropyl | Melting point 139–142 |
| 31 | $CH_3$ | $CH_3$ | 3-$CH_3$ | H | H | CO—(2,3-dihydrofuryl) | Melting point 139–158 |
| 32 | $CH_3$ | $CH_3$ | 3-$CH_3$ | H | H | $COCH_2OC_2H_5$ | Melting point 90–95 |
| 33 | $CH_3$ | $CH_3$ | 3-$CH_2OCH_3$ | H | H | $COCH_2OCH_3$ | Resin |

| Compound No. | $R_1$ | $R_2$ | $R_3$ | $R_4$ | $R_5$ | $R_6$ |
|---|---|---|---|---|---|---|
| 34 | H | H | H | H | H | $COCH_2OCH_2CH=CH_2$ |
| 35 | $CH_3$ | $CH_3$ | H | H | H | $COCH_2OCH_2CH=CH_2$ |
| 36 | $CH_3$ | $CH_3$ | H | H | H | $COCH_2OCH_2C\equiv C-CH_3$ |
| 37 | H | H | H | H | H | $COCH_2SCH_3$ |
| 38 | $CH_3$ | $CH_3$ | H | H | H | $COCH_2SCH_3$ |

It is assumed that the following compounds can be prepared accordingly.

| Compound No. | $R_1$ | $R_2$ | $R_3$ | $R_4$ | $R_5$ | $R_6$ |
|---|---|---|---|---|---|---|
| 39 | $CH_3$ | $CH_3$ | H | H | H | $COCH_2OCH_2C\equiv CH$ |
| 40 | $CH_3$ | $CH_3$ | 3-$CH_3$ | 5-$CH_3$ | H | $COCH_2OCH_2C\equiv CH$ |
| 41 | $CH_3$ | $CH_3$ | 3-Cl | H | H | $COCH_2OCH_2C\equiv CH$ |
| 42 | $CH_3$ | $NO_2$ | H | H | H | $COCH_2OCH_2C\equiv CH$ |
| 43 | $CH_3$ | Cl | H | H | H | $COCH_2OCH_2C\equiv CH$ |
| 44 | $CH_3$ | H | 5-$CH_3$ | H | H | $COCH_2OCH_2C\equiv CH$ |

The compounds of the formula A:

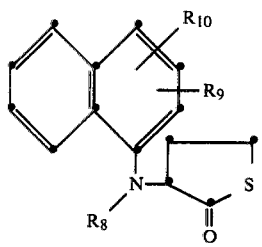

indicated below can be prepared analogously.

| Compound No. | $R_8$ | $R_9$ | $R_{10}$ | m.p. [°C.] |
|---|---|---|---|---|
| 2.1 | $COCH_2OCH_3$ | 2-$CH_3$ | H | |
| 2.2 | $COCH_2OCH_3$ | 2-$CH_3$ | 3-$CH_3$ | 140–144° |
| 2.3 | H | 2-$CH_3$ | 3-$CH_3$ | 81–84° |
| 2.4 | $COCH_2OCH_3$ | 2-$C_2H_5$ | 3-$C_2H_5$ | |
| 2.5 | $COCH_2OCH_3$ | 2-$C_2H_5$ | H | |
| 2.6 | —CO—(2,3-dihydrofuryl) | 2-$CH_3$ | H | |
| 2.7 | —CO—(2,3-dihydrofuryl) | 2-$CH_3$ | 3-$CH_3$ | |

| Compound No. | R8 | R9 | R10 | m.p. [°C.] |
|---|---|---|---|---|
| 2.8 | COCH$_2$OCH$_2$—C≡C—CH$_3$ | 2-CH$_3$ | H | |
| 2.9 | COCH$_2$OCH$_2$CH=CH$_2$ | 2-CH$_3$ | H | |
| 2.10 | COCH$_2$OCH$_2$CH=CH$_2$ | 2-CH$_3$ | 3-CH$_3$ | |

It is assumed that the following compounds can be prepared accordingly.

| Compound No. | R8 | R9 | R10 |
|---|---|---|---|
| 2.11 | COCH$_2$OCH$_2$—C≡CH | 2-CH$_3$ | H |
| 2.12 | COCH$_2$OCH$_2$—C≡CH | 2-CH$_3$ | 3-CH$_3$ |
| 2.13 | COCH$_2$OCH$_2$—C≡CH | 2-NO$_2$ | H |
| 2.14 | COCH$_2$OCH$_2$—C≡CH | 2-CH$_3$ | 4-NO$_2$ |

What is claimed is:

1. A process for the preparation of a 3-(N-arylamino)-tetrahydrothiophen-2-one derivative of the general formula A:

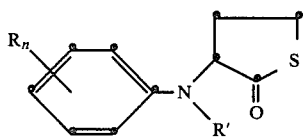

(A)

in which the heterocyclic five-membered ring is unsubstituted or monosubstituted or polysubstituted by C$_1$–C$_4$-alkyl, n is an integer from 0 to 5, R signifies a number, of identical or different substituents other than hydrogen, selected from C$_1$–C$_{12}$-alkyl, C$_1$–C$_{12}$-alkoxy, halogen, nitro, and —CH$_2$—X—R″, and whereby two substituents R which are adjacent to one another may also form together with the phenyl ring a naphthyl group, and X is oxygen or sulfur and R″ is unsubstituted, monosubstituted or polysubstituted C$_1$–C$_{12}$-alkyl, unsubstituted, monosubstituted or polysubstituted phenyl or unsubstituted, monosubstituted or polysubstituted benzyl and in the three cases mentioned the possible substituents independently of one another are selected from the series lower alkyl, lower alkoxy, halogen or nitro, and R′ is hydrogen or the group —CO—R‴, in which R‴ is a non-halogenated aliphatic, heterocyclicaliphatic or heterocyclic radical or in which R″ is an aromatic or araliphatic radical which is unsubstituted or substituted in the aromatic moiety by halogen and in which the heterocyclic structure in each case contains one or more N, O and/or S atoms and an aliphatic chain can be interrupted one or more times by oxygen, sulfur, or nitrogen, and comprises reacting a compound of the formula B:

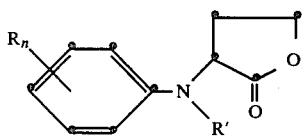

(B)

in which the possible substituents are as defined under formula A, at temperatures of +15° to +200° C. in an organic solvent with a salt of a thiocarboxylic acid.

2. A process according to claim 1, wherein the reaction is carried out at a temperature of +50° to +200° C.

3. A process according to claim 1, wherein the reaction is carried out at a temperature of +100° to +150° C.

4. A process according to claim 1, wherein the solvent is a polar, aprotic solvent.

5. A process according to any one of claims 1, 2, 3 or 4, wherein the reaction is carried out in the presence of a phase transfer catalyst.

6. A process according to any one of claims 1 or 4, wherein the reaction is carried out in the presence of a solvent which has been rendered absolutely dry.

7. A process according to any one of claims 1, 2, 3 or 4, wherein the reaction is carried out under the atmosphere of an inert gas.

8. A process for the preparation, according to claim 1, of a 3-(N-anilino)-tetrahydrothiophen-2-one derivative of the formula I:

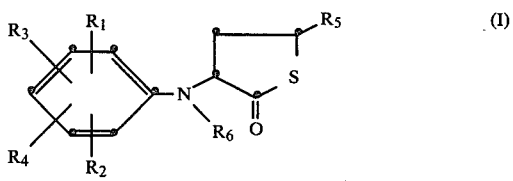

(I)

in which R$_1$ is hydrogen, C$_1$–C$_4$-alkyl, C$_1$–C$_4$-alkoxy or halogen, R$_2$ is hydrogen, C$_1$–C$_4$-alkyl, C$_1$–C$_4$-alkoxy, halogen or nitro, R$_3$ is hydrogen, C$_1$–C$_4$-alkyl, C$_1$–C$_4$-alkoxy, halogen or the group CH$_2$—X—R$_8$, in which R$_8$ is C$_1$–C$_4$-alkyl, phenyl or benzyl and X is oxygen or sulfur and R$_4$ is hydrogen or C$_1$–C$_4$-alkyl, R$_5$ is hydrogen and R$_6$ is hydrogen or the group —CO—R$_7$, in which R$_7$ is a saturated or unsaturated aliphatic hydrocarbon radical which has not more than 4 carbon atoms or is an alkylthioalkyl or alkoxyalkyl group having 2 to 5 carbon atoms, a 2-furyl or 2-tetrahydrofuryl group which is substituted by halogen or unsubstituted, or a 1,2,4-triazolylmethyl or cyclopropyl group, which comprises reacting a 3-(N-anilino)tetrahydrofuran-2-one derivative of the formula II:

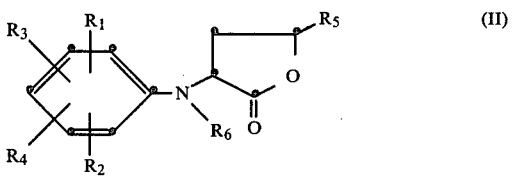

(II)

in which R$_1$, R$_2$, R$_3$, R$_4$, R$_5$ and R$_6$ are as defined under formula I, with a thiocarboxylic acid salt of the formula III:

R—COSX    (III)

in which R is a substituted or unsubstituted alkyl or aryl group and X is a metal ion or an ammonium ion.

9. A process according to claim 8, wherein X is an alkali metal cation or alkaline earth metal cation.

10. A process according to claim 8, wherein X is NH$_4^⊕$, NH$_3$(alkyl)$^⊕$, NH$_2$(alkyl)$_2^⊕$, NH(alkyl)$_3^⊕$ or N(alkyl)$_4^⊕$, in which the alkyl moiety contains 1 to 12 carbon atoms.

11. A process according to claim 8, wherein R in formula III is C$_1$–C$_6$-alkyl.

* * * * *